(12) United States Patent
Glassman et al.

(10) Patent No.: US 6,743,417 B2
(45) Date of Patent: Jun. 1, 2004

(54) METHOD OF TREATING ONYCHOMYCOSIS WITH UREA AND AN ANTIOXIDANT

(75) Inventors: Bradley P. Glassman, Fairfield, NJ (US); Dileep Bhagwat, Bronxville, NY (US); Daniel Glassman, Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 0 days.

(21) Appl. No.: 10/127,963

(22) Filed: Apr. 22, 2002

(65) Prior Publication Data

US 2003/0198611 A1 Oct. 23, 2003

(51) Int. Cl.$^7$ .............. A61K 6/00; A61K 7/00; A61K 7/04
(52) U.S. Cl. .................... 424/61; 424/401
(58) Field of Search .................... 424/61, 401

(56) References Cited

U.S. PATENT DOCUMENTS

| | | |
|---|---|---|
| 4,295,567 A | 10/1981 | Knudsen |
| 4,581,351 A | 4/1986 | Berke et al. |
| 5,340,836 A | 8/1994 | Reinhard et al. |
| 5,407,958 A | 4/1995 | Heath et al. |
| 5,445,823 A | 8/1995 | Hall et al. |
| 5,525,635 A | 6/1996 | Moberg |
| 5,573,765 A | 11/1996 | Reinhard et al. |
| 5,707,635 A | 1/1998 | Deckner et al. |
| 5,853,732 A | 12/1998 | Munden |
| 5,919,470 A * | 7/1999 | Valdez et al. ............. 424/401 |
| 5,968,533 A | 10/1999 | Porter et al. |
| 6,262,117 B1 | 7/2001 | Sefton |
| 6,281,239 B1 | 8/2001 | Glassman |

FOREIGN PATENT DOCUMENTS

| WO | 96/19186 | 6/1996 |
|---|---|---|
| WO | WO 96/19186 * | 6/1996 |
| WO | 98/23152 | 6/1998 |

OTHER PUBLICATIONS

Copy of U.S. patent application Ser. No. 09/998,537, filed Nov. 28, 2001 entitled "Antitoxidant Dermatological Compostion".

Copy of U.S. patent application Ser. No. 10/103,213, filed Mar. 20, 2002 entitled "Method of Treating Onychomycosis".

Friedman–Birnbaum, R. et al., "Treatment of onychomycosis: A randomized, double–blind comparison study with topical bifonazole–urea ointment alone and in combination with short–duration oral griseofulvin", *International Journal of Dermatology*, vol. 36, No. 1, pp. 67–69 (1997) (Abstract).

Gennaro, A., et al., *Remington's Parmaceutical Science*, 18th ed., pp. 1305,1310, 1317 and 1329 (1990).

Lucy, J.A., "Functional and Structural Aspects of Biological Membranes: A Suggested Stuctural Role for Vitamin E in the Control of Membrane Permeability and Stability", *Annals of the New York Academy of Sciences*, vol. 203, pp. 4–11 (Dec. 18, 1972).

Scharffetter–Kochanek, K. et al., "Photoaging of the skin from phenotype to mechanisms", *Experimental Gerontology*, vol. 35, No. 3, pp. 307–316 (May 2000).

Thiele, J. et al., "The Antioxidant Network of the Stratum corneum", *Curr Probl Dermatol.*, vol. 29, pp. 26–42 (2001).

* cited by examiner

*Primary Examiner*—Thurman K. Page
*Assistant Examiner*—S. Howard
(74) *Attorney, Agent, or Firm*—Andrea G. Reister; Covington & Burling

(57) ABSTRACT

A method of treating onychomycosis is described which includes administration of a topical formulation containing an effective amount of urea and an antioxidant to an infected area around a nail of a patient.

22 Claims, No Drawings

METHOD OF TREATING ONYCHOMYCOSIS WITH UREA AND AN ANTIOXIDANT

FIELD OF THE INVENTION

The present invention relates to methods of treating onychomycosis employing compositions with a combination of urea and an antioxidant. Onychomycosis refers to a fungal infection of the nail unit, defined as the nail matrix, bed or plate.

BACKGROUND OF THE INVENTION

Urea has been long recognized as a cosmetic ingredient in formulations acting as a humectant and moisturizer. High concentrations of urea, such as 40%, are also known to have mild, antimicrobial effect. At these strengths the antibacterial effects are said to be similar to those of antibiotics, with the further advantage that all the common organisms are susceptible and the possibility of resistant strains need not be seriously considered. There have been reports of keratolytic activity attributed to urea with the ability at high concentrations to solubilize and denature protein. Dermatological compositions containing from 21 to 40 wt-% urea for treating dry scaly skin have been described in U.S. Pat. No. 5,919,470.

Fungal infections of the nail are notoriously difficult to treat. Traditional, topical therapies cannot penetrate the nail plate, and eradicate the infection in and under the nail bed; they are useful only in milder forms of the disease. Systemic antifungal drug therapy is associated with potentially harmful side effects. Since oral antifungals are distributed throughout the entire body, systemic side effects such as elevated liver enzymes, gastrointestinal disorders and skin rashes are not uncommon and may require expensive medical intervention and laboratory tests.

Topical formulations for treating fungal infections, such as onychomycosis, have been described in U.S. Pat. No. 6,281,239B1. The method employs the use of a combination of a known antifungal agent and a tissue softening composition containing 30 to 60 wt-% urea.

We have recently found urea to be useful as the sole active ingredient in topically treating onychomycosis. This has been described in our co-pending application Ser. No. 10/103,213 of Mar. 20, 2002, which is incorporated herein by reference.

As the outermost layer of skin, the stratum corneum (SC) is continuously exposed to an oxidative environment, including air pollutants, ultraviolet radiation, chemical oxidants, and aerobic microorganisms. Human SC reveals characteristic antioxidant and protein oxidation gradients with increasing antioxidant depletion and protein oxidation towards the outer layers. SC antioxidants, lipids, and proteins are oxidatively modified upon treatments with ultraviolet A/ultraviolet B, ozone, and benzoyl peroxide. Thiele J. J., Schroeter C., Hsieh S. N., Podda M., Packer L., *Curr Probl Dermatol.* 2001;29:26–42.

Furthermore, the skin is increasingly exposed to ambient UV-irradiation thus increasing its risk for photooxidative damage with long term detrimental effects like photoaging, which is characterized by wrinkles, loss of skin tone, and resilience. Scharffetter-Kochanek K, Brenneisen P, Wenk J, et al., *Exp Gerontol.* 2000; 35:307–316

We have also recently described in a co-pending application topical products containing a combination of an antioxidant and a high concentration of urea which provide added efficacy and suitability for treating and protecting skin. Co-pending application Ser. No. 09/998,537 of Nov. 28, 2001 is incorporated herein by reference.

SUMMARY OF THE INVENTION

The present invention relates to methods of treating onychomycosis employing compositions containing urea as the antifungal agent. The present invention relates to methods for treating onychomycosis in humans using a combination of a safe and effective amount of urea, and from about 0.1 to about 20 wt-% of an antioxidant in a suitably defined formulation. These methods include topically administrating to the nail area of a human a safe and effective amount of the above combination. Onychomycosis refers to a fungal infection of the nail unit, defined as the nail matrix, bed or plate.

Accordingly, the present invention is a method for treating onychomycosis by topically administering a composition containing from about 10 to about 60 wt-% urea; from about 0.1 to about 20 wt-% of an antioxidant, and the balance being dermatologically acceptable excipients.

DETAILED DESCRIPTION OF THE INVENTION

The present invention is a method for treating or preventing onychomycosis. Such method includes administering to the nail area of a human in need of such treatment or prevention, a safe and effective amount of a composition including urea, for example, from about 10 to 60 wt-%, preferably about 30–50 wt-%, and particularly about 40 wt-%, and from about 0.1 to about 20 wt-% of an antioxidant.

The term "administering" as needed herein refers to any method which, in sound medical practice delivers the urea and the antioxidant to be treated in such a manner so as to be effective in the treatment of onychomycosis. Preferably, the urea and antioxidant are administered topically in a single composition.

The phrase "safe and effective amount", as used herein, means an amount of urea and antioxidant sufficient enough to significantly and positively modify the condition to be treated but low enough to avoid serious side effects, within the scope of sound medical advice. The safe and effective amount of the urea and antioxidant of the present invention will vary with the particular condition being treated, the severity of the condition, the duration of treatment, the particular pharmaceutically acceptable carriers utilized, and the like factors within the knowledge and expertise of the attending physician.

The method of the present invention typically involve administering the urea and antioxidant in an amount to cover the affected area. The specific preferred quantity of the urea and antioxidant depends upon the nature of the fungus and other skin or nail conditions also present.

The method of the present invention typically involves administering the composition in an amount to cover the affected area.

Thus for example, the dosing of the agents includes up to 720 days of administration of a pharmaceutical composition of the present invention.

For the method of the present invention, the duration of administration of the urea and antioxidant will vary according to the specific extent of the onychomycosis being treated, but typically is within the range of 90 to 210 days.

Topical Antifungal Agents

Typically, a topical antifungal agent consists of known naturally-occurring, synthetic or semi-synthetic composition, or mixture thereof, which is safe for use in the methods of the present invention, and is effective in killing or substantially inhibiting the growth of fungi, including but not limited to dermatophytes or yeast, Epidermophyton, Microsporum, Trichophyton and *Candida albicans*, and others.

Antifungal agents known to be useful for the treatment of onychomycosis include but are not limited to: topical creams, ointments, solutions, lacquers and gels containing as active agents, for example, amoroline, betadine, bifonazole, butenafine, clotrimazole, iodine, povidone iodine, econazole nitrate, isoconazole, ketoconazole, miconazole nitrate, naftifine hydrochloride, oxiconazole, sulfanazole, terbinafine, ticonazole, tolnaftate, undecenoates and ciclopirox. The above antifungal topical compositions are known to those skilled in the art.

We have found urea to be an antifungal agent of equal potency to known antifungal agents. Urea was long known for tissue softening and treating dry skin, without the need of traditional preservatives.

Thus, the present invention provides a method of treating onychomycosis in a topical composition containing urea as the antifungal agent. The purpose of an antioxidant in an antifungal composition is two fold:

Decrease the potential amount of oxygen available to the fungus

To speed up the healing process and skin restoring process once the fungus is eradicated.

Various types of fungi are present everywhere in the environment. Fungi are aerobic organisms that depend on oxygen to thrive. The dark, moist surroundings created by shoes and stockings make the feet especially susceptible to fungal infection.

Most fungi are harmless until they penetrate the skin. A fungus can invade through minor cuts, or after injury or repeated irritation to the toes have caused the nail to separate from the bed.

Nail plate (NP) is very similar to the stratum corneum (SC), the outermost layer of the skin. The main differences between the NP (which is mainly keratin) and SC are that NP has much less moisture and lipids (fatty substances) and has a high sulfur content in the form of disulfide bonds. It is the disulfide bonds which provide hardness to the nail.

Both NP and SC are continually exposed to an oxidative environment, including air pollutants, ultraviolet radiation, chemical oxidants, and aerobic microorganisms. Human SC and NP reveals characteristic antioxidant and protein oxidation gradients with increasing antioxidant depletion and protein oxidation toward the outer layers. Furthermore, the skin is increasingly exposed to other oxidative effects that contribute to wrinkles, loss of tone and loss of resiliency. Although, these characteristics are harder to see in nail tissue due to its characteristics, they are the same as SC.

Once a fungi is eradicated from either the SC or NP, an antioxidant will restore and build up the skin's natural defenses. Thus, the present topical composition with an antioxidant will both eradicate fungi and modulate desquamatory skin disorders. By combining urea and an antioxidant in an antifungal solution, an environment is created where fungi cannot live.

Antioxidants include, but are not limited to, tocopherols (vitamin E), tocopherol derivatives, tocotrienols, ascorbic acid (vitamin C), ascorbic acid derivatives, carotenoids, vitamin A or derivatives thereof, butylated hydroxytoluene, butylated hydroxyanisole, gallic esters, flavonoids such as, for example, quercetin or myricetin, selenium, grape seed extract, catechins such as, for example, epicatechin, epicatechingallate, epigallocatechin or epigallocatechingallate, sulfur-containing molecules such as, for example, glutathione, cysteine, lipoic acid, N-acetylcysteine, chelating agents such as, for example, ethylenediamine tetraacetic acid or other customary antioxidants.

One antioxidant, vitamin E, is of particular interest. The term "vitamin E" includes tocopherol (vitamin E) and derivatives thereof such as, for example, $\alpha$-, $\beta$-, $\gamma$-, $\delta$-, $\epsilon$-, $\zeta_1$, $\zeta_2$, and $\eta$-tocopherol, and $\alpha$-tocopherol acid succinate. Vitamin E is known as an antioxidant and protective vitamin for phospholipids of the cell membrane. It maintains the permeability and stability of the cell membrane, *Lucy. Annals N.Y. Academy of Science* 203, p. 4 (1972). It further has been known that vitamin E has a membrane-sealing effect. In erythrocytes, the simplest cells of the human body, there has been found that vitamin E provides a protective effect for the cell membrane. As with all antioxidants, vitamin E protects cells, including, epidermal cells which are susceptible to a wide range of oxidating events.

In addition to containing a therapeutically antifungal effective amount of urea, the composition includes dermatologically acceptable excipients as described in U.S. Pat. No. 5,919,470, which patent is incorporated herein by reference. The excipients particularly include skin protectants which include a combination of semi-solid and liquid petroleum fractions. The semi-solid skin protectant is contained in about 5.5 to about 20 wt-% and includes petrolatum or a synthetic or semi-synthetic hydrocarbon of the same nature as petrolatum. Mixtures of such ingredients can also be used. The preferred semi-solid material is petrolatum, commercially available from a wide variety of sources.

The liquid portion skin protectant is a liquid petrolatum and contained in the composition in about 10 to about 20 wt-%. This material can include any synthetic or semi-synthetic oleaginous liquid fraction. A preferred embodiment is mineral oil, which is a liquid mixture of hydrocarbons obtained from petroleum.

Another preferred ingredient encompassed in the composition of the present invention is propylene glycol which may be contained up to about 5 wt-% in the composition, preferably in the range of from about 1 to about 5 wt-%.

In addition to the above embodiments, the present composition also contains dermatologically acceptable excipients, such as for example emulsifiers and thickeners. Among these are for example a $C_{16}$ to $C_{18}$ straight or branched chain fatty alcohols or fatty acids or mixtures thereof. Preferably these include cetyl alcohol, stearyl alcohol, stearic acid, palmitic acid, or mixtures thereof. Fatty acids or fatty alcohols may be present in from about 0.25 to 2 wt-%.

Another ingredient useful in the composition of the present invention may be glyceryl stearate, which is a monoester of glycerine and stearic acid, or other suitable forms of glyceryl stearate for example glyceryl stearate SE, which is a commercially available self-emulsifying grade of glycerol stearate that contains some sodium and/or potassium stearate. Glyceryl stearate may be in the composition anywhere from about 1 to about 3 wt-%.

Xanthan gum is another ingredient which may be used in the present invention. Xanthan gum is a high molecular weight heteropolysaccharide gum produced by pure-culture fermentation of a carbohydrate with *Xanthomonas campestris*. The gum is also commercially available from various sources.

As part of the dermatologically acceptable excipients, the composition includes thickeners which provide a high viscosity cream designed to remain in place upon application to the skin. Preferred thickeners include a mixture of a carbomer and triethanolamine. The mixture is combined together and added to the composition in an amount totaling anywhere from about 0.05 to 5 wt-%. Triethanolamine is purchased as Trolamine NF from BASF. The carbomers come in various molecular weights and identified by numbers. These are otherwise known as Carbopol. A preferred embodiment of the present invention is Carbopol 940. The carbomer or Carbopols are resins which are known thickening agents. They are homopolymers of acrylic acid crosslinked with an allyl ether of pentaerythritol, an allyl ether of sucrose or an allyl ether of propylene. The carbomer is present in the composition as a thickener and also is used to suspend and stabilize the emulsion. Although Carbopol 940 is preferably used in the present invention, other analogs may also be used such as carbomer 910, 2984, 5984, 954, 980, 981, 941 and 934. Carbopol ETD 2001, 2020, and 2050 and Ultrez 20 are also commercially available and can be used since they are similar in chemistry and function.

Typical compositions employed in the present invention are for example:

| Ingredient | Approximate Wt-% |
|---|---|
| urea | 40 |
| anti-oxidant | 5.0 |
| petrolatum or a synthetic or semi-synthetic hydrocarbon, or a semi-solid mixture thereof | 5.5–20 |
| liquid petrolatum or synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| water | balance |

| Ingredient | Approximate Wt-% |
|---|---|
| urea | 30 |
| anti-oxidant | 10 |
| petrolatum or a synthetic or semi-synthetic hydrocarbon, or a semi-solid mixture thereof | 5.5–20 |
| liquid petrolatum or a synthetic or semi-synthetic oleaginous liquid fraction, or a mixture thereof | 10–20 |
| $C_{16-18}$ aliphatic straight or branched chain fatty alcohol or fatty acid, or a mixture thereof | 0.25–2 |
| propylene glycol | 1–5 |
| glyceryl stearate | 1–3 |
| xanthan gum | 0.01–0.5 |
| mixture of a carbomer and triethanolamine | 0.05–30 |
| water | balance |

A typical formulation representing the particular and most preferred embodiment of the present invention is illustrated as follows:

| Ingredient | % W/W |
|---|---|
| Tocophenyl Acetate (Vitamin B) | 3.0 |
| Urea USP | 40.4 |
| Carbopol 940 | 0.20 |
| Petrolatum | 8.94 |
| Mineral oil | 7.1 |
| Glyceryl stearate | 2.88 |
| Cetyl alcohol | 1.63 |
| Propylene glycol | 2.00 |
| Xanthan gum | 0.05 |
| Trolamine | 0.10 |
| Purified water Q.S. | 100.00. |

Various compositions, e.g. creams, lotions, and gels, containing urea and an antioxidant are active at various concentrations against *Trychophyton rubrum*, a fungus typically implicated in Moccasin tinea pedis and onychomycosis.

We claim:

1. A method of treating onychomycosis comprising administering to the nail area of a patient in need thereof a composition comprising:
   about 10 to about 40 wt-% urea;
   about 0.1 to about 20 wt-% of an antioxidant;
   about 5.5 to about 20 wt-% petrolatum or a synthetic or semi-synthetic hydrocarbon, or a semi-solid mixture thereof;
   about 10 to about 20 wt-% of a liquid petrolatum or a synthetic or semi-synthetic oleaginous liquid fraction, or a mixture thereof;
   about 0.25 to about 2 wt-% of a $C_{16-18}$ aliphatic straight or branched chain fatty alcohol or fatty acid, or a mixture thereof;
   about 1 to about 5 wt-% propylene glycol;
   about 1 to about 3 wt-% glyceryl stearate;
   about 0.01 to about 0.5 wt-% xanthan gum; and
   the balance being water.

2. A method of treating onychomycosis comprising administering to the nail area of a patient in need thereof a composition comprising:
   about 10 to about 40 wt-% urea;
   about 0.1 to about 20 wt-% of an antioxidant;
   about 5.5 to about 20 wt-% petrolatum or a synthetic or semi-synthetic hydrocarbon, or a semi-solid mixture thereof;
   about 10 to about 20 wt-% of a liquid petrolatum or a synthetic or semi-synthetic oleaginous liquid fraction, or a mixture thereof;
   about 0.25 to about 2 wt-% of a $C_{16-18}$ aliphatic straight or branched chain fatty alcohol or fatty acid, or a mixture thereof;
   about 1 to about 5 wt-% propylene glycol;
   about 1 to about 3 wt-% glyceryl stearate;
   about 0.01 to about 0.5 wt-% xanthan gum;
   about 0.05 to about 30 wt-% of a mixture of a carbomer and triethanolamine; and
   the balance being water.

3. A method of treating onychomycosis, comprising:
   administering to the nail area of a patient consisting essentially of urea as the active antifungal ingredient, an antioxidant, and one more dermatologically acceptable excipients, wherein the urea is present in an amount therapeutically effective for treating onychomycosis.

4. The method of claim 3, wherein the administering step is carried out by topically applying the composition.

5. The method of claim 3, wherein the urea is present from about 30 to about 50 wt-% urea.

6. The method of claim 3, wherein the urea is present in an amount of about 40 wt-%.

7. The method of claim 3, wherein the antioxidant is selected from the group consisting of tocopherols, tocotrenols, ascorbic acid, selenium, grape seed extract, carotennoids, vitamin A, butylated hydroxytoluene, butylated hydroxyanisole, gallic esters, flavonoids, catechins, glutathione, cysteine, lipoic acid, N-acetylcysteine, ethylenediamine tetraacetic acid and mixtures thereof.

8. The method of claim 3, wherein the composition is in a topical form selected from the group consisting of cream, ointment, solution, lacquer, gel, and foam.

9. The method of claim 3, wherein the one or more dermatologically acceptable excipients are selected from the group consisting of petrolatum or a synthetic semi-synthetic hydrocarbon, or a semi-sold mixture thereof; a liquid petrolatum or a synthetic or semi-synthetic oleaginous liquid fraction, or a mixture thereof; a $C_{16-18}$ aliphatic or branched chain fatty alcohol or fatty acid, or a mixture thereof; glyceryl stearate; xanthan gum; water; and optionally a mixture of a carbomer and triethanolamine.

10. The method of claim 3, wherein the antioxidant is vitamin E.

11. The method of claim 9, wherein the petrolatum is present from about 5.5 to about 20 wt-%.

12. The method of claim 3, wherein the dermatologically acceptable excipient is propylene glycol.

13. The method of claim 12, wherein the propylene glycol is present in an amount up to about 5 wt-%.

14. The method of claim 3, wherein the composition is semi-solid at room temperature.

15. The method of claim 1, wherein the antioxidant is vitamin E.

16. The method of claim 1, wherein the antioxidant is vitamin C.

17. The method of claim 1, wherein the antioxidant is vitamin grape seed extract.

18. The method of claim 2, wherein the antioxidant is vitamin E.

19. The method of claim 2, wherein the antioxidant is vitamin C.

20. The method of claim 2, wherein the antioxidant is vitamin grape seed extract.

21. The method of claim 3, wherein the antioxidant is vitamin C.

22. The method of claim 3, wherein the antioxidant is grape seed extract.

* * * * *